(12) United States Patent
Fogg

(10) Patent No.: US 10,466,679 B1
(45) Date of Patent: Nov. 5, 2019

(54) SYSTEM AND METHOD FOR GENERATING ELECTRICAL SIGNALS

(71) Applicant: Harold T. Fogg, Aurora, CO (US)

(72) Inventor: Harold T. Fogg, Aurora, CO (US)

( * ) Notice: Subject to any disclaimer, the term of this patent is extended or adjusted under 35 U.S.C. 154(b) by 0 days.

(21) Appl. No.: 16/053,039

(22) Filed: Aug. 2, 2018

Related U.S. Application Data

(62) Division of application No. 14/940,356, filed on Nov. 13, 2015, now Pat. No. 10,067,498.

(51) Int. Cl.
*G05B 19/408* (2006.01)
*G06F 17/50* (2006.01)

(52) U.S. Cl.
CPC ..... *G05B 19/4083* (2013.01); *G06F 17/5009* (2013.01); *G05B 2219/32343* (2013.01)

(58) Field of Classification Search
CPC ................ G05B 19/00; G05B 19/4083; G05B 2219/32343
See application file for complete search history.

(56) References Cited

U.S. PATENT DOCUMENTS

| 9,597,003 B2 | 3/2017 | Cadick |
| 9,901,259 B2 | 2/2018 | Fogg |
| 2015/0002446 A1* | 1/2015 | Ayzenberg .............. G06F 3/044 345/174 |

* cited by examiner

*Primary Examiner* — Quoc D Hoang
(74) *Attorney, Agent, or Firm* — Dan Shifrin; Shifrin Patent Law

(57) ABSTRACT

A wireless remote control panel for a signal generator is provided. The control panel comprises: a touch screen configured to display frames and accept programming values input from a user. The data fields comprise: an identification of a shape to be inserted into a sequence of wave shapes; a width of the shape; a period comprising the shape; a number of repetitions of the period; and a reference to a next frame. The control panel further comprises: a processor configured to convert the programming values into programming signals; and an output port configured to wirelessly transfer the programming signals to a function generator configured to generate a user-readable representation of the sequence of wave shapes.

16 Claims, 4 Drawing Sheets

TABLE I

| FRAME | SHAPE | | | PERIOD (ms) | RATE (bpm) | REPS | NEXT FRAME |
|---|---|---|---|---|---|---|---|
| | SHAPE VALUE | AMPL. | WIDTH | | | | |
| 1 | A1 | | | 400 | 150 | 2 | 3 |
| 2 | | | | | | | |
| 3 | B2 | | | 1000 | 60 | 2 | +2 |
| 4 | | | | | | | |
| ... | | | | | | | |
| N-1 | | | | | | | |
| N | | | | | | | 1 |

FIG. 3

| FRAME | SHAPE | | | PERIOD (ms) | RATE (bpm) | REPS | NEXT FRAME | STATISTICS |
|---|---|---|---|---|---|---|---|---|
| | SHAPE VALUE | WIDTH (ms) | AMPL. (mV) | | | | | |
| 1 | A1 | 200 | 4 | 400 | 150 | 2 | 3 | 2 beats |
| 2 | | | | | | | | |
| 3 | B2 | 500 | 2 | 1000 | 60 | 2 | +2 | 2 beats |
| 4 | | | | | | | | |
| ... | | | | | | | | |
| N-1 | | | | | | | | |
| N | | | | | | | 1 | |

TABLE II

FIG. 4

SYSTEM AND METHOD FOR GENERATING ELECTRICAL SIGNALS

RELATED APPLICATION DATA

The present application is a divisional application of and claims the benefit of commonly-owned co-pending U.S. application Ser. No. 14/940,356 entitled PHYSIOLOGICAL ELECTRICAL SIGNAL SIMULATOR, filed on Nov. 13, 2015, which application is incorporated herein by reference in its entirety. The present application is also related to commonly-owned co-pending U.S. application Ser. No. 14/708,226 entitled SYSTEM AND METHOD FOR SEARCHING, WRITING, EDITING, AND PUBLISHING WAVEFORM SHAPE INFORMATION, filed on May 9, 2015, which application is incorporated herein by reference in its entirety. The present application is also related to commonly-owned co-pending U.S. application Ser. Nos. 16/053,053 and 16/053,059, both entitled PHYSIOLOGICAL SIGNAL STIMULATOR AND SIMULATOR, and both filed on the filing date hereof, which applications are incorporated herein by reference in their entireties.

TECHNICAL FIELD

The present invention pertains generally to electrical signal generation products such as arbitrary waveform generators and, in particular, to an apparatus and method for stimulating biological activity and simulating biological process signals, such as ECG signals.

BACKGROUND ART

When designing signal generation products, it is common practice to define waveform shapes with digital data files that contain values proportional to values of analog data to be generated by a digital-to-analog converter (DAC) driven by the digital data. The amplitude of digital values may be increased or decreased to meet system requirements or user preferences, and the number of samples may be decreased by skipping samples or increased by inserting more samples using methods appropriate for the application. Typically, frequency is controlled by adjusting the digital sampling rate. Amplitude is typically controlled by adjusting a multiplying factor applied to analog values or digital values or to both analog and digital values.

Often, when preparing to generate a waveform signal, users select a shape, a width for the shape, an amplitude for the shape and a frequency or rate at which the signal is to be generated. For example, the Fogg System Model 310 ECG Simulator has controls for selecting a shape, a width for the shape, an amplitude for the shape and a rate at which the signal is to be generated. There are a variety of methods used to define waveform sequences comprising many shapes and many periods of time in many arrangements to produce many signal sequences for the representation of many events for which the capability of signal generators is applicable. The design and management of waveform sequences is complicated, and one objective is to simplify the process of designing, managing and generating waveform sequences.

SUMMARY OF THE INVENTION

In one embodiment, an apparatus is provided for generating electrical signals for stimulating a system under test (SUT). The apparatus comprises: a remote control panel configured to receive programming values and output programming signals; and a function generator. The function generator comprises: a communication port configured to receive the programming signals from the control panel; a memory configured to store instructions and predetermined values; a processor configured to process the programming signals and predetermined values according to the instructions stored in the memory; a digital-to-analog converter (DAC) configured to convert the processed signals into analog output signals; an output port configured to make the analog output signals available to the SUT; and an input port configured to receive second signals from the SUT.

In another embodiment, a wireless remote control panel is provided for a signal generator. The control panel comprises: a touch screen configured to display frames and accept programming values input from a user. The data fields comprise: an identification of a shape to be inserted into a sequence of wave shapes; a width of the shape; a period comprising the shape; a number of repetitions of the period; and a reference to a next frame. The control panel further comprises: a processor configured to convert the programming values into programming signals; and an output port configured to wirelessly transfer the programming signals a function generator configured to generate a user-readable representation of the sequence of wave shapes.

In another embodiment, an electrocardiograph (ECG) simulator is provided to generate sequences of wave shapes having specified average rates for a sequence of varying rates.

In still another embodiment, a system is provided for combining frames in a plurality of ways to provide as output a new frame comprising a function of the combined frames.

In another embodiment, a system is provided for combining a plurality of frames to provide as output a new frame that generates a specified average period as a function of the periods of the combined frames.

In another embodiment, a method is provided for generating electrical signals for stimulating a system under test (SUT). The method comprises: receiving programming values in a remote control panel; outputting programming signals from the remote control panel; receiving in a function generator the programming signals from the control panel; storing instructions and predetermined values in a memory in the function generator; processing the programming signals and predetermined values according to the instructions stored in the memory; converting the processed signals into analog output signals; and outputting the analog output signals available to the SUT.

BRIEF DESCRIPTION OF THE DRAWINGS

FIG. 3 is a table representing one possible arrangement of data fields displayed on the panel of FIG. 2; and FIG. 4 is a table representing another possible arrangement of data fields displayed on the panel of FIG. 2.

DETAILED DESCRIPTION OF THE PREFERRED EMBODIMENT

Definitions

To aid in understanding the present invention, the following list of terms and their meanings is included. The meaning of the terms, as set forth below, is the intended meaning whenever the term is used herein, unless another meaning is believed to be clear from the context.

Amplitude: The vertical interval in specified units from a baseline such as the x-axis in an x-y coordinate system; for applications herein, the intervals are typically represented by dimensionless numbers that are expected to be scaled using whatever units are appropriate for the application such as, for example, electrical units for voltage and current.

Field: A part of a data base record representing an item of data, as for example, the data in a cell identified by the intersection of a row identified for a Frame and of a column identified for the field.

Frame: (noun) A supporting structure that contains parts with spaces between them and used to build something; a single cycle of shapes in a string of repeated shapes; (verb) to construct or compose a statement or code used to generate a waveform sequence; formulate the essentials of a complex thing, idea, etc.

Period: An interval during which an event of interest occurs; the time required for one repetition of a shape; if the shape has a specified width, the shortest period for one repetition is the specified width; the longest period is limited by the system that generates it.

Shape: Something such as a mold or pattern used to give or determine form; when applied to generating waveforms herein, it is understood that an identified shape inherently includes values for amplitude and width which are expected to be multiplied by scaling factors chosen to produce desired results for generated waveforms.

Width: The horizontal interval in specified units in an x-y coordinate system from the beginning to the end of a shape identified by a shape value; as applied herein, horizontal intervals are typically represented by dimensionless numbers that are expected to be scaled using whatever units are appropriate for the application such as, for example, length, time, or frequency.

The described features, structures, or characteristics of the invention may be combined in any suitable manner in one or more embodiments. In the following description, numerous specific details are provided to provide a thorough understanding of embodiments of the invention. One skilled in the relevant art will recognize, however, that the invention can be practiced without one or more of the specific details, or with other methods, components and so forth. In other instances, well-known structures, materials, or operations are not shown or described in detail to avoid obscuring aspects of the invention.

Figure 1:
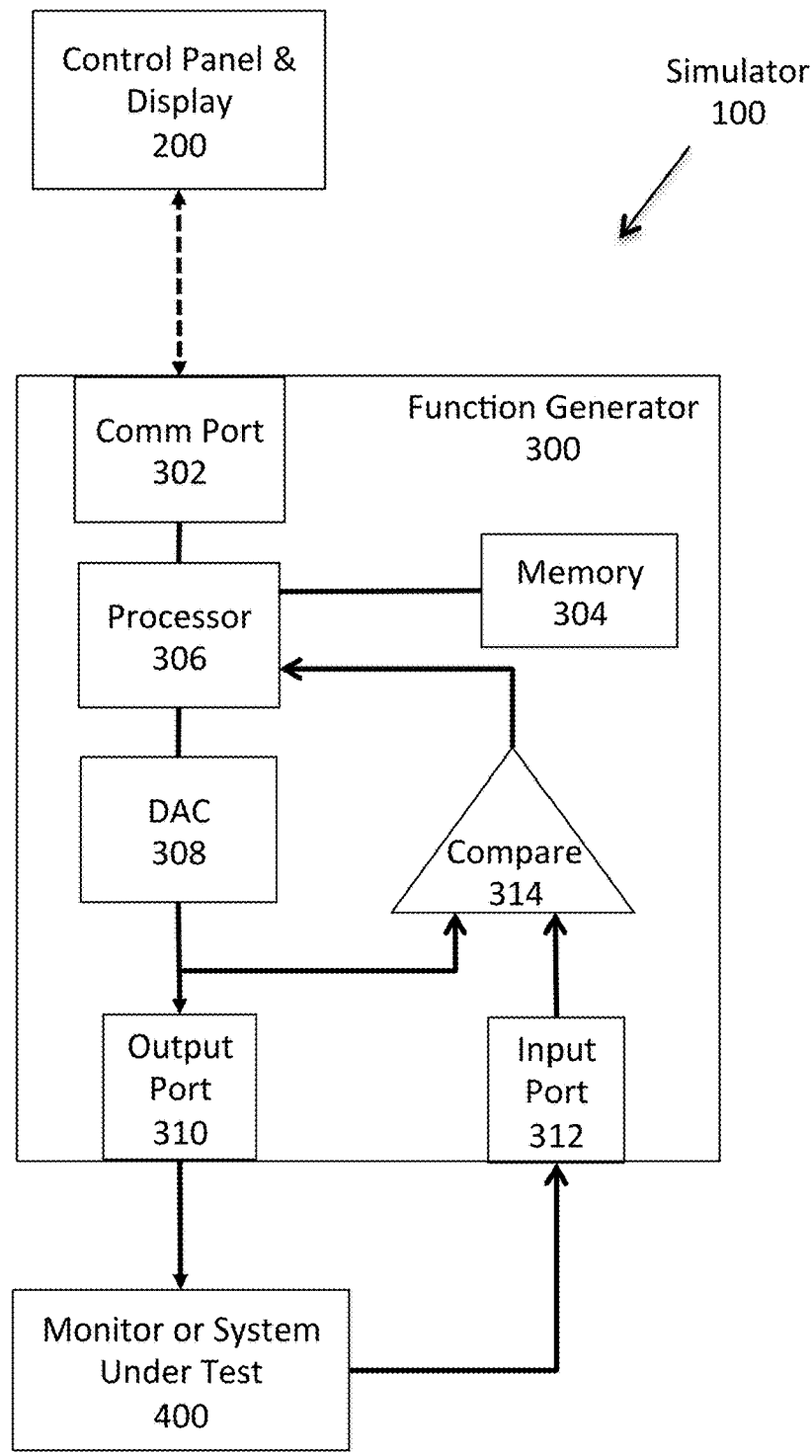
FIG. 1 is a block diagram of an embodiment of a physiological electrical signal simulator of the present invention.

The present invention provides an apparatus and method for simulating or stimulating physiological electrical signals, such as electrocardiograph (ECG) signals. FIG. 1 is a block diagram of an embodiment of a physiological electrical or biological signal simulator 100 of the present invention. The simulator 100 generally includes a control and display panel 200, and a function generator 300 for outputting signals to a system under test (SUT) 400, such as an ECG or other biological signal monitor. The panel 200 and function generator 300 may be connected through a wired connection or, preferably, wirelessly using methods such as that provided by WiFi and Bluetooth® technology. In such a configuration, the panel 200 may thus be used remotely.

The function generator 300 may include a communication (comm) port 302 configured to receive programming signals from the control panel 200, a memory 304 configured to store instructions and predetermined values, a processor 306 configured to process the programming and predetermined values according to the instructions stored in the memory, a digital-to-analog converter (DAC) 308 configured to convert the processed values into analog output signals, and an output port 310 configured to make the analog output signals available to the SUT 400. As will be described in more detail, the function generator 300 may also include an input port 310 to receive signals from the SUT 400 and a comparator 314 configured to compare the signals from the SUT 400 against the signals from the DAC 308. A comparison of the signals may then be displayed on the panel 200.

Figure 2:
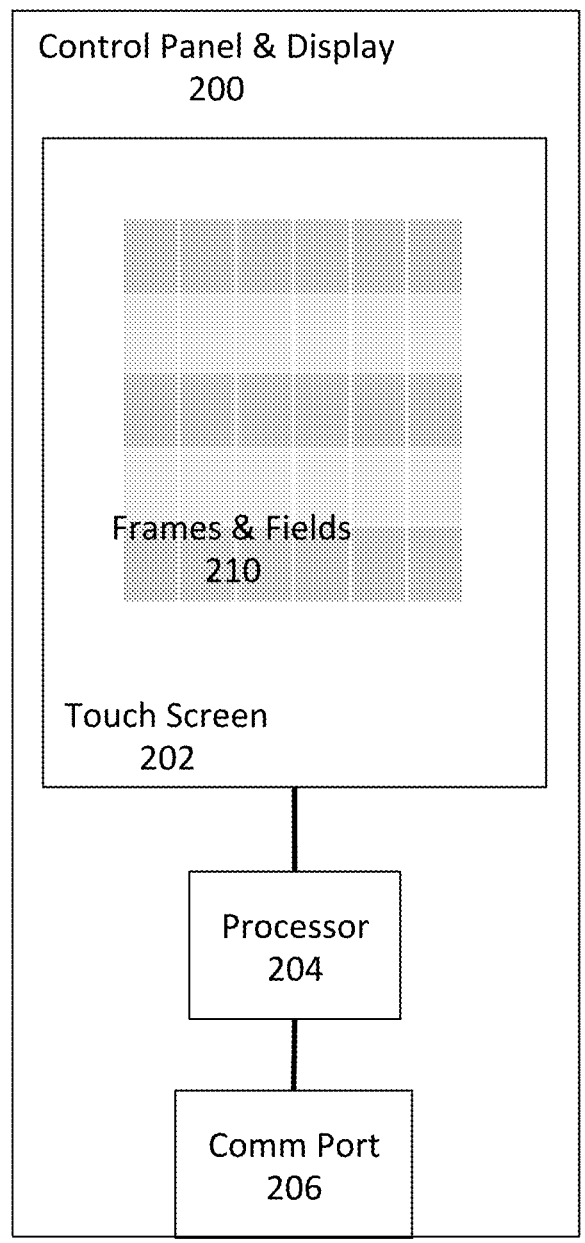
FIG. 2 illustrates an embodiment of the remote control panel and display which is part of the simulator of FIG. 1.

The panel 200 may be part of any appropriate input product, such as a computer, tablet computer, or smart phone, to receive programming values from a user, output programming signals to the function generator 300, and receive signals for display from the function generator 300. Referring to FIG. 2, the panel 200 may include a processor 204, configured to receive signals from the touch screen 202 and convert them into programming signals, and a comm port 206, configured to transfer the programming signals to the comm port 302 of the function generator 300. The processor 204 is also configured to receive signals from the comm port 302 of the function generator 300 for display on the panel 200. Preferably, the panel 200 will include a touch screen 202 which is configured to display frames 210, accept input values from a user, and display information from the function generator 300. In some embodiments, information from the function generator 300 may be displayed on a screen or hard-copy printout separate from the panel 200. In some other embodiments, some or all of the operations of the function generator 300 may be incorporated into components of the panel 200.

TABLE I of FIG. 3 is a representation of one possible arrangement of frames 210 displayed on the panel 200 of FIG. 2. TABLE II of FIG. 4 is a representation of another possible arrangement of frames 210 displayed on the panel 200 of FIG. 2. Although the frames 210 are shown in table format, they may also be presented or displayed to a user in any other appropriate format.

When the panel 200 includes a touch screen 202, each of the displayed fields may be configured as a "button" which the user may select, then edit information using a keypad or, alternatively, make a selection from a drop-down list or scrollable "wheel" of possible entries.

Referring to TABLE I of FIG. 3, each entry in the "SHAPE" column represents a value identifying a predefined shape that is stored in the memory 304. In addition to being defined by the type of shape itself (e.g., sine, triangular, etc.), each predefined shape has an inherent default amplitude and width. TABLE I may provide frames 210 in which values for the amplitude and width may be edited to preferred values for the width and amplitude of the shape. The PERIOD defines the time interval during which one repetition of the shape is generated. RATE is defined as the number of times the shape is generated during a specified interval of time and is inversely proportional to the PERIOD. If the shape represents one event such as one heart beat, the rate may be calculated in units of beats-per-minute (BPM) from Rate (in BPM)=60,000/Period (in milliseconds). The REPS (repetitions) define the number of times the Period will be repeated for the Frame.

The NEXT FRAME value points to the number of the next frame to be inserted into the sequence. NEXT FRAME may be the actual frame number or may be an increment/decrement pointer. For example, in frame 1 of TABLE I, NEXT FRAME equals 3, indicating that the next frame to be inserted into the sequence is frame 3. In frame 3, NEXT FRAME equals+2, indicating that the next frame to be inserted is 3+2=5. Thus, a number with a plus sign (+) would indicate that the next frame is "below" the current frame in TABLE I; a number with a negative sign (−) would indicate that the next frame is "above" the current frame in TABLE I; and, an unsigned number indicates an absolute frame number. If the NEXT FRAME cell, other than in the last frame N, is blank, NEXT FRAME will default to a predetermined value, such as +1. If the NEXT FRAME cell in the last frame N is blank, NEXT FRAME will default to a predetermined action, such as repeat the sequence from frame 1, proceed through the just-ended sequence in the reverse order, stop, or some other action. In TABLE I, NEXT FRAME=1 in the last frame N, indicating that the sequence should return to frame 1 and repeat. In some embodiments, each of the fields may allow a referenced input, as described above with respect to inputs to the NEXT FRAME field, such that the value of a frame may be incremented, decremented, or remain the same with respect to the entry for the previous frame. For example, in TABLE I, the RATE in frame 3 may be entered as −90, indicating that the RATE will be 90 beats per minute less than the RATE of the previous frame (frame 1). In some other embodiments, the value of a field may vary within the frame. For example, the RATE within a frame may vary with each REP of the frame.

The length of a frame may be increased, such as by inserting a specified number of members, each member having a specified value, or may be decreased, such as by removing a specified number of members.

TABLE II of FIG. 4 provides some additional input fields. The WIDTH field allows entry of a desired shape width and the AMPLITUDE field allows entry of the shape amplitude. Additional fields may be included to enter or display notes and statistics for information about the frame such as expected number of detectable events (for example, the number of expected beats), average period, the average signal value, the maximum or minimum amplitude, and the frequency content of signals in the frame.

If desired, a sequence of frames, such as illustrated in the Tables, may be saved as a new defined "shape," which may be subsequently entered by name when creating a new sequence. Any parameter of the saved sequence may be modified and either saved with the newly created sequence, saved separately as still another new sequence, or saved as a modification to the originally saved sequence. Additionally, if a parameter in a saved sequence is changed, the change may be applied to each other sequence that incorporates or references the saved sequence.

Frames may be combined in a number of different ways, providing a new frame that is a function of the combined frames. Some examples include:
  a) combining frames by multiplying their values, whether the frames are of equal or unequal lengths;
  b) combining frames by a process of convolution;
  c) combining frames by a process of correlation;
  d) combining frames by a process of auto-correlation;
  e) combining a frame with itself to provide a spectrum of the frame;
  f) combining frames to provide a specified average period of the periods of the individual frames;
  g) combining frames to provide a specified average rate of the rates of the individual frames;
  h) combining frames by concatenation;
  i) concatenating a frame with itself; and
  j) combining frames by adding their values.

When frames are combined by adding their values, their respective lengths may be determined and, if different, their lengths may be adjusted to be equal to each other prior to adding.

When frames are combined to provide a specified average period, the specified average period may be selected as an integer or a non-integer. For convenient scaling, the specified average period may be an integer or non-integer factor of 60,000.

It is known that a normal, healthy heart beats in a manner that is not perfectly uniform. Without going into detail that is known in the medical field, healthy hearts beat with variations in the period between beats. It is therefore important for an ECG simulator to take into account such variations. An embodiment of the simulator 100, when configured as an ECG simulator, may display a varying heart rate from the function generator 300 with a predetermined average. In one embodiment, an average rate is computed by converting the average of the periods into a rate (in beats-per-minute, as described above). The average may be taken over a specified period of time (such as, for example, four seconds) or over a specified number of beats (such as, for example, four beats).

The simulator 100 may transmit simulated physiological electrical (biological process) signals to a monitor, in place of signals from patient electrodes, for the purpose of evaluating, verifying, and validating various functions of the monitor. When the monitor is an ECG monitor, such functions may include those related to variations in heart rate. As noted above, the comparator 314 is configured to compare the signals from the monitor or SUT 400 against the signals from the DAC 308 and a comparison of the signals may then be displayed on the panel 200. In this manner, the SUT 400 may be evaluated to help decide whether corrective action is required.

The description of the present invention has been presented for purposes of illustration and description, but is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated.

What is claimed is:

1. A system for generating programming signals representing a sequence of electrical signal wave shapes, comprising:
  a wireless remote control panel, comprising:
    a touch screen on which a sequence of frames is displayed, each frame comprising a plurality of buttons representing programming values to be entered or edited by a user on the touch screen, the values comprising:
      an identification of a shape to be inserted into a sequence of wave shapes;
      a width of the shape;
      a period comprising the shape;
      a number of repetitions of the period; and
      a reference to a next frame;
    a processor configured to combine the programming values of the sequence of frames into programming signals representing a corresponding sequence of wave shapes; and
    an output port configured to wirelessly transfer the programming signals to a function generator in which a user-readable representation of the sequence of wave shapes is generated from the programming signals.

2. The system of claim 1, wherein a length of a frame is increased by inserting a specified number of members, each member having a specified value.

3. The system of claim 1, wherein a length of a frame is decreased by removing a specified number of members.

4. The system of claim 1, wherein the sequence of frames is displayed as a table, each frame comprising a row of the table and each value comprising a column of the table.

5. The system of claim 1, wherein a value comprising a reference to a next frame comprises a reference to any other frame in the sequence of frames.

6. The system of claim 1, wherein a value comprising an identification of a shape comprises an identification of a previously defined shape.

7. The system of claim 6, wherein previously defined shape comprises a previously saved sequence of frames.

8. The system of claim 1, wherein the processor is further configured to combine the programming values of the sequence of frames by a process selected from the group consisting of:
   a) combining frames by multiplying their values;
   b) combining frames by convolution;
   c) combining frames by correlation;
   d) combining frames by auto-correlation;
   e) combining a frame with itself to provide a spectrum of the frame;
   f) combining frames to provide a specified average period of the periods of the individual frames;
   g) combining frames to provide a specified average rate of the rates of the individual frames;
   h) combining frames by concatenation;
   i) concatenating a frame with itself; or
   j) combining frames by adding their values.

9. A method for generating programming signals representing a sequence of electrical signal wave shapes, comprising:
   displaying a sequence of frames on a wireless remote control panel, each frame comprising a plurality of buttons representing programming values to be entered or edited by a user on the touch screen, the values comprising:
      an identification of a shape to be inserted into a sequence of wave shapes;
      a width of the shape;
      a period comprising the shape;
      a number of repetitions of the period; and
      a reference to a next frame;
   combining the programming values of the sequence of frames into programming signals representing a corresponding sequence of wave shapes; and
   wirelessly transferring the programming signals to a function generator in which a user-readable representation of the sequence of wave shapes is generated from the programming signals.

10. The method of claim 9, further comprising increasing a length of a frame by inserting a specified number of members, each member having a specified value.

11. The method of claim 9, further comprising decreasing a length of a frame removing a specified number of members.

12. The method of claim 9, further comprising displaying the sequence of frames as a table, each frame comprising a row of the table and each value comprising a column of the table.

13. The method of claim 9, wherein a value comprising a reference to a next frame comprises a reference to any other frame in the sequence of frames.

14. The method of claim 9, wherein a value comprising an identification of a shape comprises an identification of a previously defined shape.

15. The method of claim 14, wherein previously defined shape comprises a previously saved sequence of frames.

16. The method of claim 9, further comprising combining the programming values of the sequence of frames by a process selected from the group consisting of:
   a) combining frames by multiplying their values;
   b) combining frames by convolution;
   c) combining frames by correlation;
   d) combining frames by auto-correlation;
   e) combining a frame with itself to provide a spectrum of the frame;
   f) combining frames to provide a specified average period of the periods of the individual frames;
   g) combining frames to provide a specified average rate of the rates of the individual frames;
   h) combining frames by concatenation;
   i) concatenating a frame with itself; or
   j) combining frames by adding their values.

* * * * *